United States Patent [19]
Han et al.

[11] Patent Number: 5,976,560
[45] Date of Patent: Nov. 2, 1999

[54] VEGETABLE DERIVED PETROLEUM JELLY REPLACEMENT

[76] Inventors: Nam Fong Han; Xiao Ying Zhang, both of 21 Antares Drive, Unit 123-124, Nepean, Ontario, Canada, K2E 7T8

[21] Appl. No.: 09/116,101

[22] Filed: Jul. 15, 1998

[30] Foreign Application Priority Data

Jan. 30, 1998 [CA] Canada .................................. 2225352

[51] Int. Cl.⁶ ............................... A61K 7/00; A61K 7/42; A61K 9/00; A61K 31/355
[52] U.S. Cl. ........................... 424/401; 424/59; 424/400; 514/458; 514/770; 514/778; 514/844; 508/101; 508/136
[58] Field of Search ............................ 424/59, 400, 401; 514/458, 770, 778, 844; 508/101, 136

[56] References Cited

U.S. PATENT DOCUMENTS

| | | |
|---|---|---|
| 4,393,043 | 7/1983 | Koulbanis et al. . |
| 4,424,164 | 1/1984 | Bliznak et al. ........................ 106/150 |
| 4,437,895 | 3/1984 | Koulbanis et al. . |
| 4,765,978 | 8/1988 | Abidi et al. ............................... 424/80 |
| 4,804,532 | 2/1989 | Busch, Jr. . |
| 4,837,011 | 6/1989 | Macchio et al. . |
| 4,948,521 | 8/1990 | Stewart, Jr. et al. ..................... 252/28 |
| 5,156,876 | 10/1992 | Clapp et al. ............................ 426/609 |
| 5,229,130 | 7/1993 | Sharma et al. . |
| 5,444,096 | 8/1995 | McCrea et al. . |
| 5,478,385 | 12/1995 | Washbourne . |
| 5,510,100 | 4/1996 | Picard et al. . |
| 5,510,409 | 4/1996 | Romano . |
| 5,552,135 | 9/1996 | Cioca et al. . |
| 5,582,818 | 12/1996 | Nakanishi et al. . |
| 5,595,965 | 1/1997 | Wiggins . |
| 5,614,481 | 3/1997 | Lopez Rangel ......................... 508/485 |
| 5,618,850 | 4/1997 | Coury et al. .......................... 514/772.2 |
| 5,622,690 | 4/1997 | Potter et al. . |
| 5,647,899 | 7/1997 | Lightcap, Jr. . |
| 5,662,937 | 9/1997 | McCuaig . |
| 5,674,853 | 10/1997 | Forse et al. . |
| 5,679,361 | 10/1997 | Pradier et al. . |

FOREIGN PATENT DOCUMENTS

| | | |
|---|---|---|
| 1244350 | 11/1988 | Canada . |
| 2065011 | 2/1991 | Canada . |
| 2032940 | 6/1991 | Canada . |
| 2049430 | 2/1992 | Canada . |
| 2130450 | 9/1993 | Canada . |
| 2100030 | 1/1994 | Canada . |
| 2141102 | 7/1995 | Canada . |
| 2147089 | 10/1995 | Canada . |
| 2161285 | 4/1996 | Canada ........................... A61K 7/00 |
| 2163843 | 6/1996 | Canada . |
| 2171237 | 10/1996 | Canada . |
| WO 95/11663 | 5/1995 | WIPO . |

*Primary Examiner*—Shelley A. Dodson
*Assistant Examiner*—Marina Lamm
*Attorney, Agent, or Firm*—Kohn & Associates

[57] ABSTRACT

The present invention is a replacement for petroleum jelly as a base for products suitable for application to the skin. It is comprised of vegetable oil and silica. The vegetable oil is preferably a canola oil and more preferably a high oleic acid/low linolenic acid canola oil. The silica is preferably untreated fumed silica powder. The vegetable oil is preferably present in the range of 50–90% and most preferably 80%. The silica is present in the range of 5–15% and most preferably 10%. Other ingredients which may be added include vitamin E, margarine or butter, starch, and sunscreen. The base of the present invention has a significantly higher melting temperature than petroleum jelly.

13 Claims, 2 Drawing Sheets

VEGETABLE DERIVED PETROLEUM JELLY REPLACEMENT

FIELD OF THE INVENTION

The present invention relates to the field of products suitable for application to the skin and, in particular, to a replacement for petroleum jelly as a base for such products.

BACKGROUND OF THE INVENTION

Products which are applied to the skin such as cosmetics or lotions often use petroleum jelly as a base. Petroleum jelly is inexpensive, abundant, and can be smoothly applied to the skin. However, petroleum jelly has a number of disadvantages. In particular, petroleum jelly has a low melting temperature and begins to liquify at approximately 38° C.(100° F.). When petroleum jelly-based products are placed in the sun particularly during the summer months, they can reach temperatures which causes the petroleum jelly to liquify or "melt". Temperatures in the summer may reach 100° F. or higher in some areas of North America or in such locations as in a car or a window. When the petroleum jelly-base liquifies, the remaining ingredients will separate out from the base and thus drastically reduce the shelf life of the product.

In recent years, more skin care products are available which utilize natural oils and ingredients in place of petroleum jelly. Examples of such products are disclosed in Canadian Patent 1,244,350 issued Nov. 8, 1988 for a skin care and shaving composition; Canadian patent application 2,161,285 published Apr. 26, 1996 disclosing a cosmetic composition; and Canadian Patent Application 2,130,450 published Sep. 2, 1993 disclosing insect repellent. Each of these references is directed towards products adapted for application to the skin and incorporate natural oils. However, these natural oils are not suitable as a general replacements for petroleum jelly but rather are disclosed in specific mixtures in products applied to skin. These products also do not overcome the disadvantages of a petroleum jelly base such as a low melting temperature and resulting reduced shelf life.

U.S. Pat. No. 5,679,361 issued Oct. 21, 1997 and discloses a solid or pasty make-up composition. The composition is comprised of a fatty phase and a pulverulent phase. The fatty phase is 20–70% by weight of the total weight of the composition. The pulverulent phase is a light powder which is present in an amount of 5–30% by weight of the total composition. This patent is directed towards a process for preparing the make-up composition. In this process, the powder is used for the processing and pressing of the composition and reacts with the other ingredients in the make-up to form a final product. The fatty phase may incorporate a vegetable oil. This composition provides a product with an improved feel on application but it does not provide for a product with a raised melting point or a product which will not separate out on heating.

There therefore is a need for a general replacement for petroleum jelly as a base for products for application to skin which has a higher melting point and which does not cause the skin care product to separate out into its constituent ingredients on minimal heating.

There is also a need for a replacement for petroleum jelly suitable for use in a variety of products. Further, there is a need for a replacement which is derived from natural ingredients such as plant products including vegetable oils.

SUMMARY OF THE INVENTION

It is therefore an object of the present invention to overcome the disadvantages of the prior art and to provide a replacement for petroleum jelly as the base in products suitable for application to the skin.

It is also an object of the present invention to provide a composition which has a higher melting point than petroleum jelly. It is a further object of the present invention to provide a composition which incorporates natural oils.

There, therefore, is provided a base for a product suitable for application to skin or a lubricant composition, said base comprising vegetable oil and silica.

BRIEF DESCRIPTION OF THE DRAWINGS

Preferred embodiments of the present invention will now be described and may be better understood when read in conjunction with the following figures in which.

DETAILED DESCRIPTION OF THE INVENTION

Figure 1:
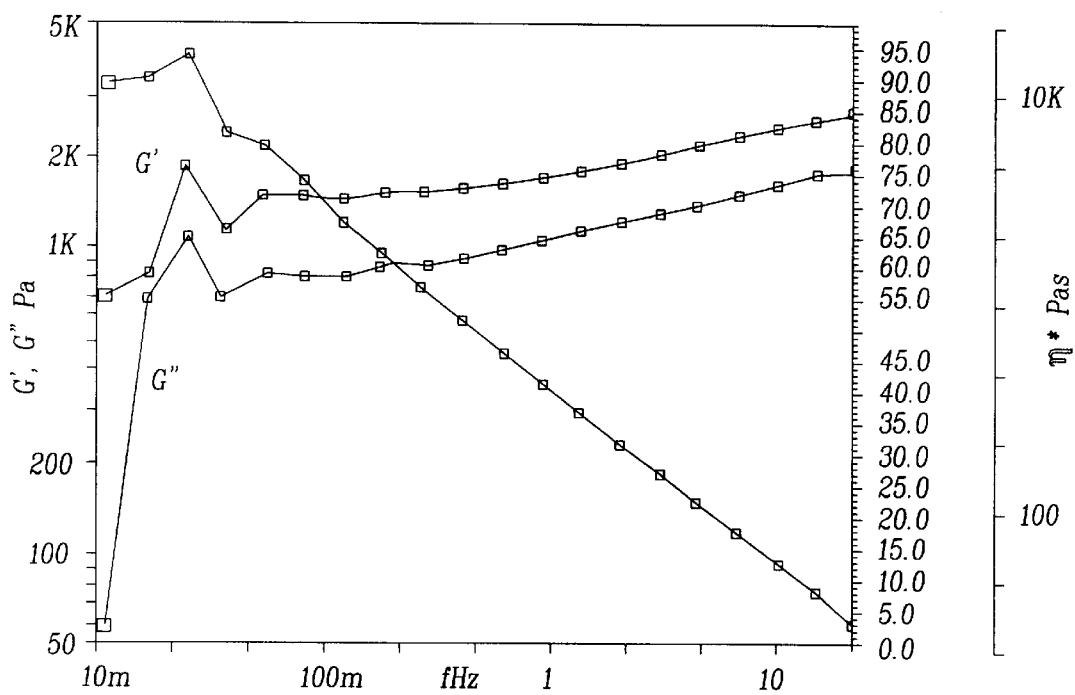
FIG. 1 is a graph of the oscillation curve for the canola gel base of Example 1 showing G', G", and dynamic viscosity versus frequency.

The present invention provides a replacement for petroleum jelly comprising a mixture of vegetable oil and silica.

The composition of the present invention preferably includes vegetable oil in an amount in the range of approximately 50%–90% by weight of the total composition. Silica is preferably present in an amount of approximately 5%–15% by weight of the total composition. In a preferred embodiment, vegetable oil is present in an amount of approximately 80% by weight of the total composition and silica in an amount of approximately 10% by weight of the total composition.

Additional ingredients may be added to the present invention to improve its suitability as a base for a skin care product. Other preferred ingredients which may optionally be added to the present invention include vitamin E, margarine or butter, starch, sunscreen, and fragrance. Obviously, many other ingredients are commonly added to compositions to formulate a skin care product and these would be acceptable additions to the present invention.

Vegetable oils are defined as oils derived from plants. They include, as a group, the glyceryl esters of fatty acids including those which have been hybrided or hydrogenated to reduce or eliminate unsaturation or triglycerides. Also included are synthetic prepared esters of glycerin and fatty acids. They have the structure:

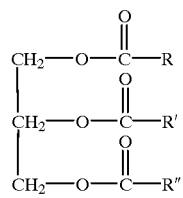

in which —COR, —COR', —COR" may be the same or different fatty acid radicals.

Suitable vegetable oils include all vegetable oils including hydrogenated vegetables oils. These vegetable oils may be selected from, but are not limited to, canola oil, sunflower oil, soybean oil, corn oil, cottonseed oil, olive oil, wheat germ oil, borage oil, evening primrose oil, black currant oil, linseed oil, peanut oil, and safflower oil.

Preferably, canola oil is used in the present base composition. Preferred canola oil includes modified canola oil having an increased amount of oleic acid and a decreased amount of linolenic acid than that present in oil derived from naturally occurring canola. Preferred high oleic acid canola oils are those in which the acid moieties comprise a minimum of 80% oleic acid. These oils preferably contain a reduced amount of linolenic acid in the range of 0-3%. These oils have a higher stability than oil derived from naturally occurring canola. Such high oleic acid canola oil may be obtained from the Brassica species. It is commercially available, for example, from DowElanco Canada Inc.

The silica present in the composition of the present invention is in a powder form and may be silica powder or silicone dioxide powder. In particular, untreated fumed silica powder is preferred. Such fumed silica powder preferably has a surface area of approximately 200±25 $m^2/g$ and has an average particle (aggregate) length of 0.1 to 0.6 microns. Preferably, the average particle length is 0.2 to 0.3 microns.

Vitamin E may be included in the base of the present invention. It is preferably present in an amount in the range of 0 to 1% of the total weight of the composition. More preferably, it is present in an amount of approximately 0.1% by weight. Preferably, tocopherols and its derivatives are used and, more preferably, dl-alpha-tocopherol.

Margarine or butter may also be present. It is preferably present in an amount in the range of 0 to 40% by weight of the total composition. More preferably, it is present in the amount of 30% by weight. It is preferable to use soybean margarine in the composition of the present invention. It is also preferably to include vitamin E when including margarine or butter to reduce any rancidity.

Starch is a further optional ingredient in the composition of the present invention. It is preferably present in an amount in the range of 0 to 15% by weight of the total composition. Preferably, corn starch is used.

Sunscreens are preferably present in an amount in the range of 0 to 15% by weight of the total composition. The preferred amount is approximately 7% by weight. Sunscreens include those as defined in the FDA Regulatory Book 21 CFR Part 352, 700 and 740 dated Apr. 5, 1994. Any recognized sunscreen may be used and preferred sunscreens include octyl methoxycinnamate, octyl salicylate and titanium dioxide.

No water is added to the present composition. The presence of water would cause the composition to become unstable and therefore unsuitable for its intended use.

To obtain a base having a desired viscosity, the amount of silica added to the vegetable oil is varied. The order of addition of the ingredients of the present invention is not essential and they may be added in any desired order. Further, the ingredients are added at ambient temperatures and do not require heating.

The silica is added to the vegetable oil by agitation and is absorbed by the oil. This absorption causes the viscosity of the vegetable oil to increase. To produce a base which is more viscous and "gel-like", a higher amount of silica is added than to produce a base which has a lower viscosity and is more "liquid-like".

FIGS. 1 to 4 show the oscillation curves and creep recovery curves for the canola gel base outlined in following Examples 1 and 4. The curves indicate that all of the test samples have characteristic gel-like structures. The results shown in the figures result from rheological tests determined on a Bohlin rheometer at 25° C. (See *Industrial Rheology*, Philip Sherman, Academic Press, 1970.)

Figure 3:
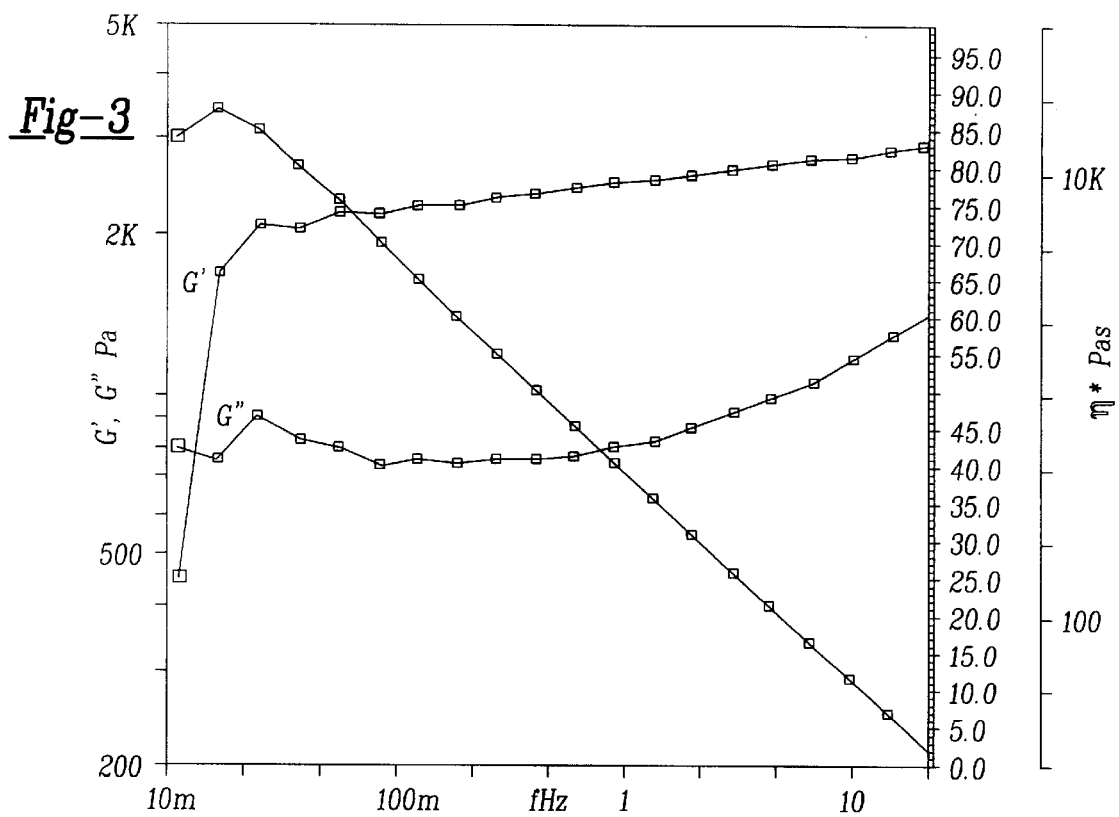
FIG. 3 is a graph of the oscillation curve for the canola gel base of Example 4 showing G', G", and dynamic viscosity versus frequency.

In FIGS. 1 and 3, the graphs plot G', G", and dynamic viscosity against Frequency where G' is the storage modulus representing gel structure and G" is the loss modulus representing the flow property of the system. The plot of dynamic viscosity versus frequency indicates that as frequency increases, the viscosity decreases. Further, the value of G' is greater than G" in both systems. Thus, the test samples have a gel-like structure.

Figure 2:
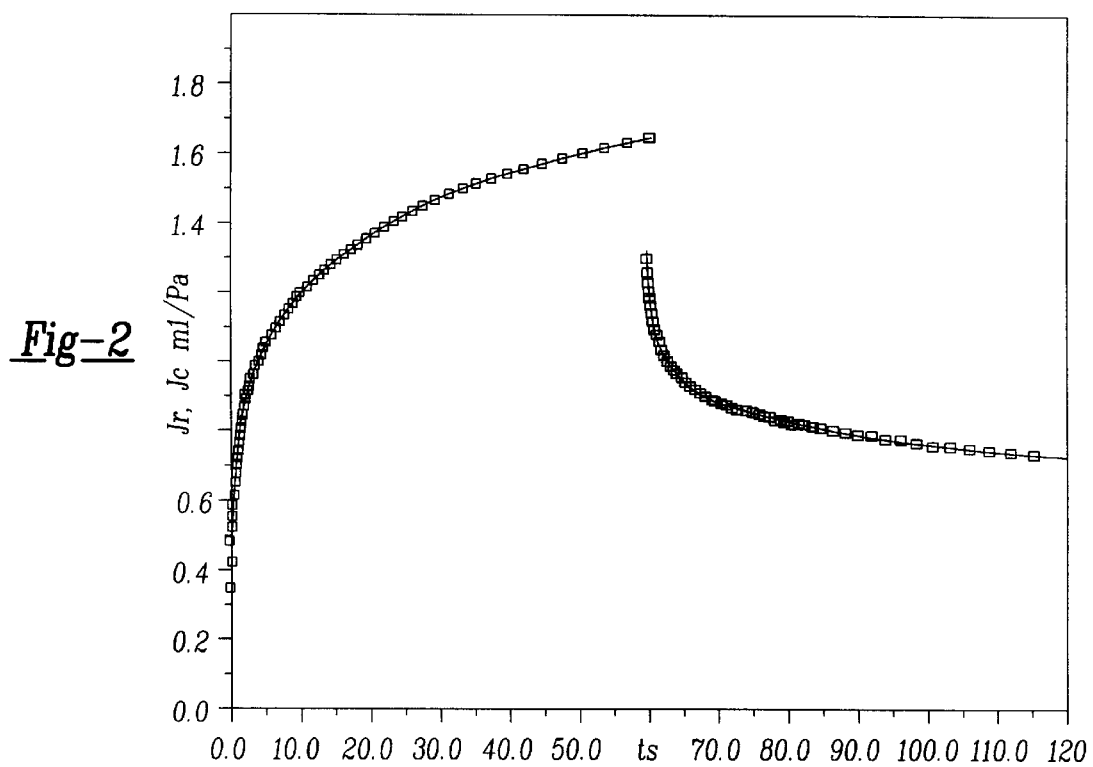
FIG. 2 is a graph of the creep recovery curve for the canola gel base of Example 1.
Figure 4:
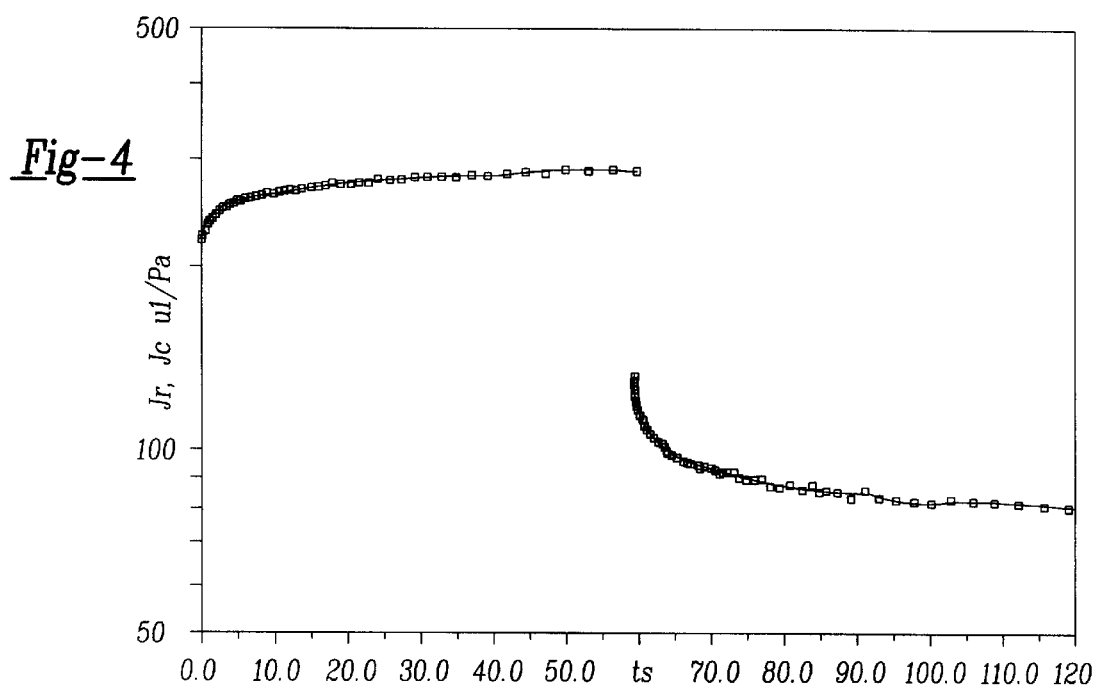
FIG. 4 is a graph of the creep recovery curve for the canola gel base of Example 4.

In FIGS. 2 and 4, compliance is plotted against time measured in seconds. Compliance is a measurement of the ratio of strain over applied stress. The graphs in FIGS. 2 and 4 indicate that the test samples have characteristic properties of a gel-like structure.

The base composition of the present invention has a melting temperature at or above approximately 75° C.(170° F.) which is substantially higher than the melting temperature of a petroleum jelly base. Therefore, the base of the present invention does not liquify under normal temperatures or when left out in the sun. As well, since it retains its structure, it does not cause the product to separate out into its constituent ingredients and therefore need to be discarded.

The composition of the present invention may be used as a replacement for petroleum jelly as a base for products for application to the skin. It is suitable for use in any petroleum jelly-based product and may be substituted for the petroleum jelly base in the product. It may also be used as a replacement for petroleum jelly in lubricants.

Examples of base compositions of the present invention are provided hereafter along with an example of a skin care product utilizing the composition of the present invention as a base. These examples are illustrative only and are not intended to be limiting.

EXAMPLES

Example 1

A canola gel, Base 1, which employs deodorized canola oil, Vitamin E, and silica powder is provided. The gel is produced by adding the ingredients in Table 1 individually under agitation at room temperature. Weight percentages are based on the total weight of the composition.

TABLE 1

| Ingredient | Weight Percent |
|---|---|
| Deodorized canola oil[a] | 89.9% |
| Vitamin E[b] | 0.1% |
| Silica powder[c] | 10% |

[a]DowElanco Canada Inc.
[b]Hoffman-La Roche Inc. (dl-α tocopherol)
[c]Cabot Corporation Add ingredient 2 into ingredient 1 at room temperature under agitation. With constant mixing, slowly sift in ingredient 3. Mix until homogeneous.

Example 2

A canola gel, Base 2, which employs deodorized canola oil, soy margarine, Vitamin E and silica powder is provided. The gel is produced in a similar manner to Example 1, by adding the ingredients in Table 2 under agitation.

TABLE 2

| Ingredient | Weight Percent |
| --- | --- |
| Deodorized canola oil | 61.9% |
| Soy margarine[d] | 30% |
| Vitamin E | 0.1% |
| Silica powder | 8% |

[d]Golden Gate Michca Inc.

Add ingredient 2 (previously melted) into ingredient 1 at room temperature under agitation. Add ingredient 3 into the mixing phase of ingredients 1 and 2. With constant mixing, slowly sift in ingredient 4 into the mixture. Mix until homogeneous.

Example 3

A canola gel, Base 3, which employs deodorized canola oil, soy margarine, Vitamin E, titanium dioxide, silica powder, and corn starch is provided. The gel is produced by adding the ingredients according to the weight percentages shown in Table 3.

TABLE 2

| Ingredient | Weight Percent |
| --- | --- |
| Deodorized canola oil | 71.8% |
| Soy margarine | 10% |
| Vitamin E | 0.1% |
| Titanium dioxide[e] | 0.1% |
| Silica powder | 10% |
| Corn starch[f] | 8% |

[e]Degussa Corporation
[f]Casco Inc.

Add ingredients 1, 2 and 3 as in Example 2. With constant mixing, slowly sift ingredient 4 into the mixing phase. Mix until uniform and slowly sift in ingredient 5 and then ingredient 6. Mix until homogeneous.

Example 4

A canola gel, Base 4, which employs deodorized canola oil, Vitamin E, silica powder, and corn starch is provided. The gel is produced by individually adding the ingredients in Table 4 under agitation at room temperature. Weight percentages are based on the total weight of the composition.

TABLE 4

| Ingredient | Weight Percent |
| --- | --- |
| Deodorized canola oil | 81.8% |
| Vitamin E | 0.2% |
| Silica powder | 10% |
| Corn starch | 8% |

Add ingredient 2 into ingredient 1 at room temperature with agitation. With constant mixing, slowly sift in ingredient 3 and then ingredient 4. Mix until homogeneous.

Example 5

A cosmetic preparation in the form of a moisturizing cream which employs the canola gel bases of the invention is provided. The moisturizing cream is produced by combining the ingredients of phase A, B, C, D and E given in Table 5 where weighted percentages are based on the total weight of the compositions.

TABLE 5

| Ingredient | Weight Percent |
| --- | --- |
| Phase A | |
| Deionized water | 84.6% |
| Carbomer 934NF | 0.3% |
| Phase B | |
| Glycerin | 1.0% |
| Triethanolamine | 0.1% |
| Phase C | |
| Sorbitan monostearate | 1.0% |
| Isopropyl myristate | 2.0% |
| Cetyl palmitate | 2.0% |
| Coco-caprylate/caprate | 2.0% |
| Cetyl alcohol | 1.0% |
| Stearic acid | 2.0% |
| Canola gel, Base 1 | 3.0% |
| Phase D | |
| Diazolidinyl urea + propylene glycol + methyl paraben + propyl paraben | 0.2% |
| Phase E | |
| Fragrance | 0.3% |

Phase A ingredients are combined with a Lightnin™ mixer while being heated to 75° C. Combine ingredients in Phase B and then add Phase B to Phase A. Phase C ingredients are combined and heated until melted at 75° C. in a separate container. Add the melted Phase C to the mixing Phase AB with constant agitation. The mixing Phase ABC is then cooled to 40° C., and, at this temperature, add the ingredients in Phase D and Phase E one at a time into the mixture.

The present invention relates to a base to be used in products such as that outlined in Example 5. However, it can easily be incorporated into other final products including, but not limited to, moisturizers, cosmetics, and suntan lotions.

The above-described embodiments of the present invention are meant to be illustrative of preferred embodiments of the present invention and are not intended to limit the scope of the present invention. Various modifications, which would be readily apparent to one skilled in the art, are intended to be within the scope of the present invention. The only limitations to the scope of the present invention are set out in the following appended claims.

We claim:

1. A base for a product suitable for application to skin, the base comprising vegetable oil in an amount in the range of about 50–90% by weight, untreated fumed silica powder in an amount in the range of about 5 to 15% by weight, margarine or butter in the amount of about 0.1 to 40% by weight, and starch in the amount of about 0.1 to 15% by weight, the base being anhydrous.

2. A base for a product suitable for application to skin, the base comprising vegetable oil in an amount in the range of about 50–90% by weight, untreated fumed silica powder in an amount in the range of about 5 to 15% by weight, margarine or butter in the amount of about 0.1 to 40% by weight, and starch in the amount of about 0.1 to 15% by weight, the base being anhydrous and the base made from a process comprising the step of combining the oil, silica powder, margarine or butter, and starch at about room temperature without heating.

3. The base of claim 1 wherein said vegetable oil is present in an amount of 80% by weight.

4. The base of claim 3 wherein said silica is present in an amount of 10% by weight.

5. The base of claim 1 wherein said vegetable oil is canola oil.

6. The base of claim 1 wherein said vegetable oil is high oleic acid canola oil.

7. The base of claim 1 wherein said silica has a surface area of $200\pm25 m^2/g$ and an average particle length of 0.1 to 0.6 microns.

8. The base of claim 7 wherein said average particle length is 0.2 to 0.3 microns.

9. The base of claim 1 further comprising one or more compounds selected from the group consisting of vitamin E, sunscreen, and fragrance.

10. The base of claim 9 wherein said vitamin E is present in an amount in the range of 0 to 1%.

11. The base of claim 10 wherein said vitamin E is present in an amount of 0.1%.

12. The base of claim 1 wherein said margarine or butter is present in an amount of 30%.

13. The base of claim 9 wherein said sunscreen is present in an amount in the range of 0% to 15%.

* * * * *